United States Patent

Berger et al.

Patent Number: 5,806,520
Date of Patent: Sep. 15, 1998

[54] METHOD AND DEVICE FOR EVALUATING AND CHARACTERIZING THE PROPERTIES OF BONE

[75] Inventors: Geneviève Berger, Bourg-La-Reine; Pascal Laugier, Paris, both of France

[73] Assignee: Centre National de la Recherche Scientifique (C.N.R.S.), Paris, France

[21] Appl. No.: 702,444

[22] PCT Filed: Mar. 24, 1995

[86] PCT No.: PCT/FR95/00376

§ 371 Date: Sep. 24, 1996

§ 102(e) Date: Sep. 24, 1996

[87] PCT Pub. No.: WO95/26160

PCT Pub. Date: Oct. 5, 1995

[30] Foreign Application Priority Data

Mar. 25, 1994 [FR] France .................................. 94 03555

[51] Int. Cl.⁶ ...................................................... A61B 8/00
[52] U.S. Cl. .................. 128/660.06; 128/661.03
[58] Field of Search ........................ 128/660.01, 660.06, 128/660.07, 661.03; 73/597, 599, 602; 364/413.25

[56] References Cited

U.S. PATENT DOCUMENTS

| | | | |
|---|---|---|---|
| 3,847,141 | 11/1974 | Hoop .................................... | 128/662.03 |
| 4,774,959 | 10/1988 | Palmer et al. ........................ | 128/660.06 |
| 5,343,863 | 9/1994 | Wiener et al. ...................... | 128/661.3 X |
| 5,348,009 | 9/1994 | Ohtomo et al. .................. | 128/661.03 X |

*Primary Examiner*—Francis Jaworski
*Attorney, Agent, or Firm*—Pollock, Vande Sande & Priddy

[57] ABSTRACT

A method for the in vivo evaluation and characterization of the mechanical or architectural properties of bones relies on the propagation of an ultrasound wave through the bone and subsequently studying the interaction of this wave with the bone. The bone is scanned using an ultrasound beam obtained from focused transducers. Then, the signals transmitted through the bone and/or reflected by the faces of the bone and/or scattered by the internal structures of the bone are collected. The signals obtained are stored in memory. The signals thus stored are processed for measuring: the propagation velocity of the ultrasound beam in the bone; the thickness of the bone; the transmission attenuation coefficient of the ultrasound beam; and the reflection parameters for estimating the backscatter and attenuation coefficients.

5 Claims, 10 Drawing Sheets

METHOD AND DEVICE FOR EVALUATING AND CHARACTERIZING THE PROPERTIES OF BONE

FIELD OF THE INVENTION

The present invention relates to a method for in vivo evaluation and characterization of the mechanical or architectural properties of bone, employing the ultrasound technique.

BACKGROUND OF THE INVENTION

During the past few years, ultrasound equipment has appeared on the market which makes it possible to measure attenuation and its dependence as a function of frequency (attenuation coefficient), or the propagation velocity of ultrasound in transmission through the calcaneus or the patella. These devices are essentially intended for detecting or for monitoring osteoporosis.

A number of devices providing in vivo evaluation of bone by employing ultrasound beams are already known.

Publications WO 90/01903 and WO 87/07494 describe devices which make it possible to measure the propagation velocity of ultrasound in bone by using two transducers which are placed on either side of the bone.

U.S. Pat. No. 4,774,959 describes a device which measures the transmission attenuation coefficient using a first pair of transducers, this device including a second pair of transducers which measure the thickness of the bone where the ultrasound beam has passed through the bone.

European publications 0,341,969 and 0,480,554 describe devices which make it possible to measure the transmission attenuation coefficient and the velocity of ultrasound with the aid of a pair of transducers placed face to face.

Finally, U.S. Pat. No. 4,941,474 describes an apparatus which makes it possible to analyze both signals transmitted through the bone and signals which are reflected or scattered by the internal architecture of the bone. Said apparatus comprises at least one transducer emitting an ultrasound beam through the bone, means for receiving and memorizing the signals which are transmitted through the bone or reflected by its surfaces and means for treating the stored signals in order to measure the propagation velocity of the ultrasound beam in the bone, its thickness, the transmission attenuation coefficient of the ultrasound beam and the scattering parameters. This apparatus cannot provide parametric images.

Experience derived from the use of the known apparatus mentioned above shows that the measurements which can be carried out with them remain rudimentary, and that the accuracy, sensitivity and reproducibility of these measurements need to be improved. Furthermore none of these known devices can provide parametric images.

BRIEF DESCRIPTION OF THE INVENTION

Starting from this prior art the present invention relates to a process as disclosed in U.S. Pat. No. 4,941,474 but providing parametric images, said process being characterized in that the ultrasound beam is obtained by using focused transducers and said beam is scanned along one or several directions different from the ultrasound propagation direction notably along orthogonal axes.

According to the present invention, for producing, in transmission mode, parametric images of attenuation as a function of frequency and propagation of velocity of the ultrasound, use is made of a pair of focused transducers, placed opposite one another and operating at low frequency, that is to say at a central frequency of between 100 kHz and 3 Mhz, and preferably between 100 kHz and 1 Mhz.

In its application to producing reflectivity images in echographic mode (reflection mode), the method of the present invention uses a focused transducer or a pair of focused transducers, placed opposite and capable of operating in a wider frequency range, that is to say at a central frequency of between 100 kHz and 10 MHz.

According to the present invention, for producing reflectivity images in echographic mode and for estimating the attenuation and/or back-scatter coefficients as a function of the frequency of the ultrasound beam, and also with a view to producing, in transmission, parametric images of attenuation as a function of frequency and of propagation velocity, use is made of a pair of transducers, placed opposite one another and operating at low frequency, that is to say at a central frequency of between 100 kHz and 3 MHz, preferably between 100 kHz and 1 MHz, and a focused transducer or a pair of focused transducers placed opposite one another and operating at high frequency, that is to say at a central frequency of between 1 MHz and 10 MHz.

The invention secondly relates to an apparatus making it possible to implement the method as specified hereinabove.

A device for implementing the method specified hereinabove includes means for emitting and receiving focused ultrasound, placed on opposite sides of the bone to be analyzed, and is characterized in that it comprises: means making it possible to scan the ultra-sound beam, an acquisition module including the means for emitting ultrasound and receiving the ultrasound signals after their interaction in the bone; a system for storing in memory the signals thus obtained, and a module for processing the said signals in order to estimate the acoustic parameters known for their relationship with the mechanical or viscoelastic properties of the bone.

According to one exemplary embodiment of the device forming the subject matter of the invention, use is made of focused transducers, placed opposite one another, these transducers being of the single-element type.

According to another embodiment of the present invention, the measurements may be carried out in immersion, the device then including an enclosure filled with a liquid such as water, or else these measurements can be carried out by contact with the aid of a coupling medium and by using an array of ultrasound transducers.

This device is furthermore characterized in that the module for processing the signal includes a computer, a bulk memory and a signal-processing software package designed to analyze the data originating from the acquisition module, this processing module including a set of functions making it possible, in particular, to calculate the transmission attenuation coefficient, calculate the thickness of bone passed through at the location of the measurement, calculate the propagation velocity, calculate the reflection back-scatter coefficient and calculate the reflection attenuation coefficient.

Other characteristics and advantages of the present invention will emerge from the description given hereafter with reference to the attached drawings, which illustrate various examples of implementation and embodiments thereof, without any limiting character.

DETAILED DESCRIPTION OF THE INVENTION

Figure 1:
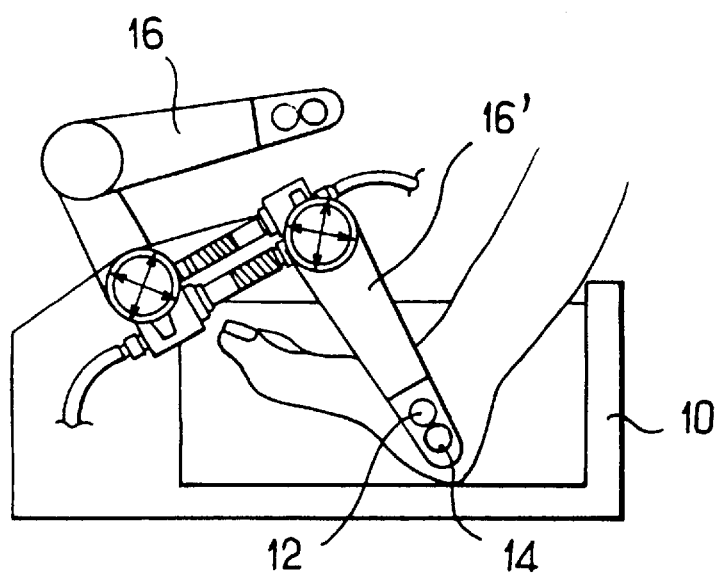
FIG. 1 is a schematic view in elevation, representing one exemplary embodiment of an apparatus for implementing the method forming the subject matter of the invention.

Referring to FIG. 1, it is seen that, in this nonlimiting exemplary embodiment, the device implementing the method forming the subject matter of the invention essentially includes an enclosure 10 filled with water, making it possible to take the measurements during immersion, the presence of the liquid medium ensuring good coupling between the radiation source and the bone, of which it is desired to evaluate, in particular, the mechanical properties. This device includes an ultrasound emission source, here consisting of pairs of focused piezoelectric ultrasound transducers, placed opposite one another on either side of the bone to be analyzed, one of the pairs of transducers such as 12 operating at high frequency, that is to say in the frequency range of from 1 MHz to 10 MHz, specified hereinabove, whereas the pair of transducers such as 14, operate at low frequency in a range of between 100 kHz and 1 MHz. These pairs of transducers are mounted on a mobile bridge which, in FIG. 1, has been represented respectively in the raised position 16 and in the position 16' lowered for measurement.

As specified hereinabove, the principle on which the method forming the subject of the invention is based resides in transmitting an ultrasound wave into the bone and in studying the interaction of this wave with the bone. The device according to the invention, illustrated by FIG. 1, can operate both in transmission and in reflection. In this exemplary embodiment, it is equipped with a conventional system for scanning the ultrasound beam, this scanning being obtained by displacement of the focused transducers under the action of two motors which displace them in a plane, along the orthogonal axes X and Y, thus allowing the entire bone volume to be explored.

The device furthermore includes an acquisition module tasked with emitting the ultrasound signals and receiving these signals after they have interacted in the bone. A system for storing in memory the signals thus obtained is also provided, as is a module for processing these signals in order to estimate certain acoustic parameters known for their relationship with the mechanical or viscoelastic properties of the bone.

The invention, in particular by virtue of automatic scanning of the ultrasound beam, provides a solution to the difficulties resulting from the use of current apparatus, in particular as regards accurate positioning of the bone for measurement and location of the region in which the measurement takes place. The invention furthermore makes it possible to carry out ultrasound measurements in transmission through the bone and in reflection. Collection of the signals reflected and/or scattered by the internal architecture of the bone provides information complementary to that already contained in the signals which have been transmitted through the bone. The device according to the invention thus makes it possible to obtain substantially more information than is obtained by devices of known types. The invention furthermore provides better precision.

As specified in the preamble of the present description, the method forming the subject matter of the invention makes it possible to obtain, in transmission mode, parametric images of attenuation as a function of frequency and of propagation velocity of the ultrasound beam, by employing a pair of focused transducers, placed opposite and operating at low frequency, that is to say at a central frequency between 100 kHz and 1 MHz.

The invention also makes it possible to produce reflectivity images in echographic mode and to obtain an estimate of the attenuation and back-scatter coefficients, by using a single focused transducer or a pair of focused transducers, placed opposite one another and operating at high frequency, that is to say at a central frequency of between 1 MHz and 10 MHz.

Finally, it is also possible, by virtue of the method of the invention, to produce reflectivity images in echographic mode and obtain an average estimate of the attenuation and/or back-scatter coefficients as a function of the frequency of the ultrasound beam, and also to produce in transmission parametric images of attenuation as a function of frequency and of propagation velocity of the ultrasound beam. In this application, the invention employs a pair of transducers, placed opposite one another and operating at low frequency, that is to say at a central frequency of between 100 kHz and 1 MHz, and a pair of focused transducers, placed opposite one another and operating at high frequency, that is to say at a central frequency of between 1 MHz and 10 MHz.

As already specified hereinabove, the device implementing the method according to the invention essentially includes an "ultrasound signal acquisition" module and a "signal processing" module.

The "acquisition" module has the functions:
- of emitting the ultrasound waves with the aid of the transducers defined hereinabove;
- of receiving the so-called reference ultrasound waves, receiving ultrasound waves transmitted through the bone, and receiving waves reflected and/or scattered by the bone and its structures;
- scanning the entire bone volume with the ultrasound beam.

This "acquisition" module is composed, as defined hereinabove, of ultrasound sources and receivers (pair of focused transducers). The ultrasound pulse thus radiated is transmitted into the propagation medium, with which it interacts. As has been specified hereinabove, the measurement can be carried out in immersion in order to obtain good coupling between the radiation source and the bone. The interaction between the propagation medium and the incident wave gives rise to a directly transmitted wave (coherent wave) and one or more waves reflected or scattered by the bone and/or its internal structures.

This "acquisition" module is furthermore composed of a stage for detection, amplification (for example automatic gain control) and analog-digital conversion of the signals, of a computer, and of a processor with its conventional environment. This part of the device is of conventional design and will consequently not be described.

This module furthermore includes, in this exemplary embodiment, the mechanical device which scans the ultrasound beam in a plane perpendicular to the direction of propagation of the ultrasound beams. During scanning, the ultrasound emitter and receiver execute the same movement synchronously, so that their relative position remains identical. This scanning is produced with the aid of two programmable motors.

Figure 2:
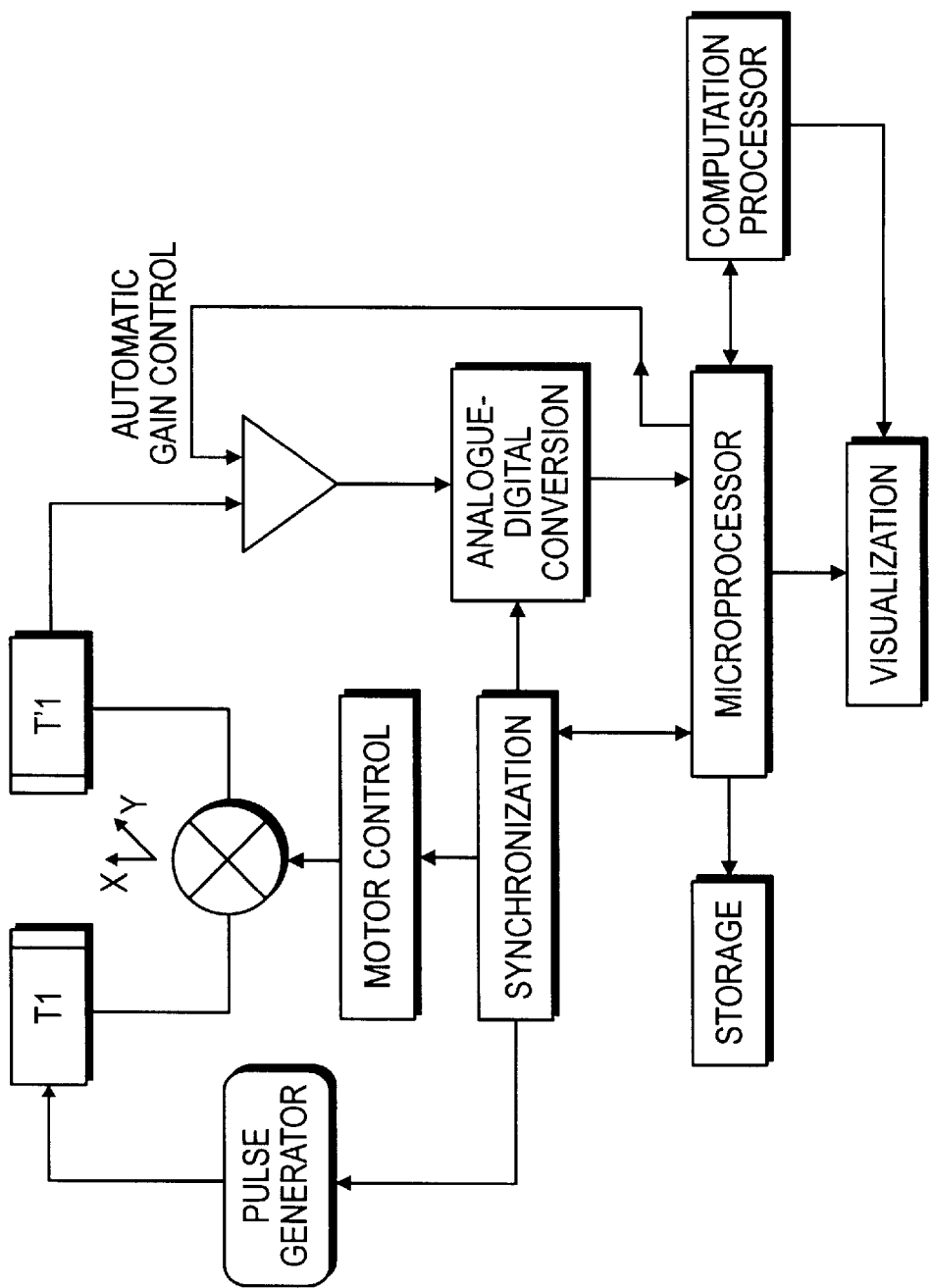
FIG. 2 is a block diagram illustrating overall the data acquisition module employed by the invention.

FIG. 2 is an overall diagram of the device according to the invention, providing operation only in transmission mode. This device includes a transducer T1 for emission, associated with a transducer T'1 for reception and arranged opposite T1. The transducers are focused, the distance separating them being approximately equal to twice the focal length. The transducer T'1 detects the waves emitted by the transducer T1 and converts them into an electrical signal which is amplified, digitized and transferred to the computer.

Figure 3:
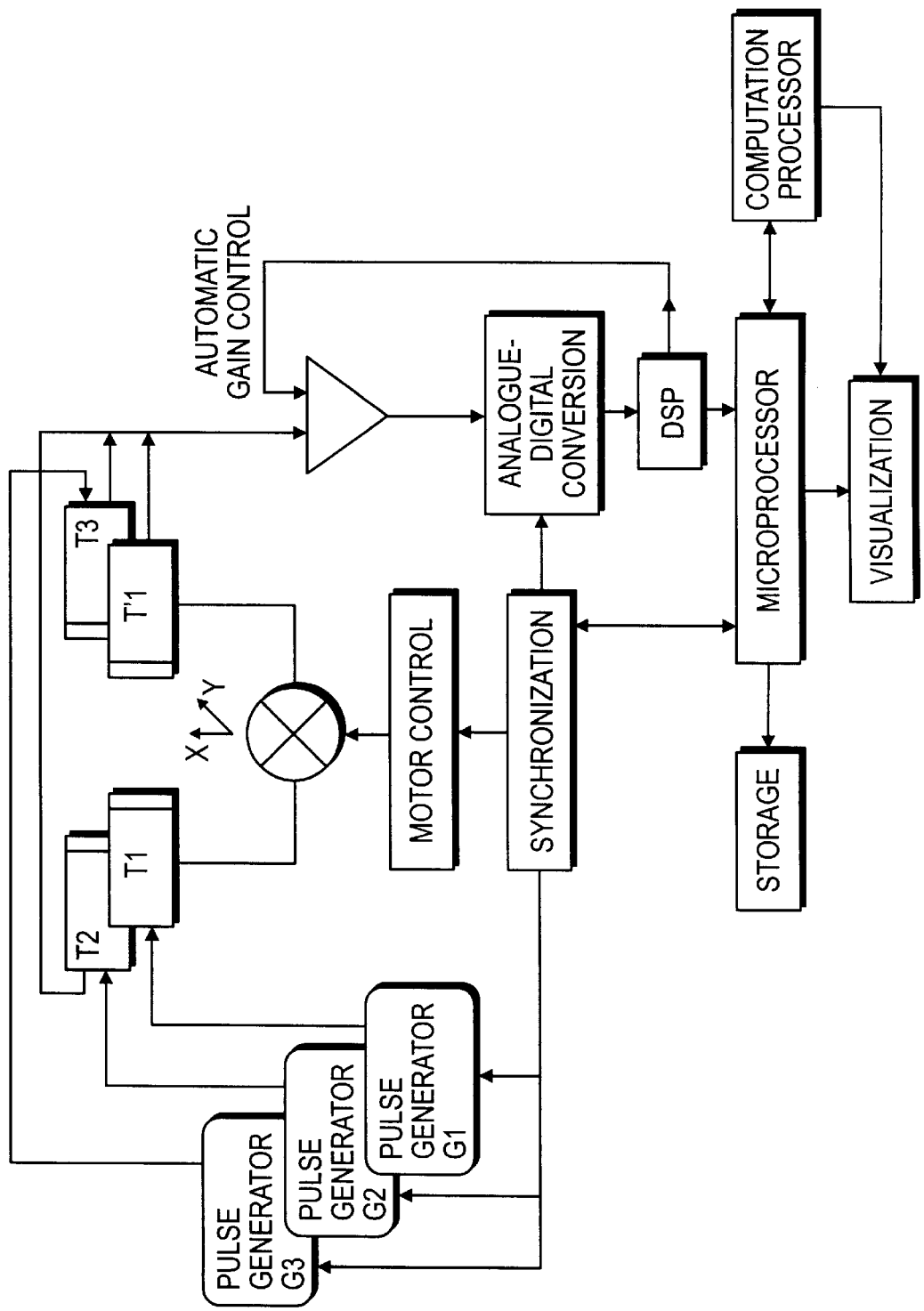
FIG. 3 is also a diagram illustrating overall an acquisition module operating simultaneously in transmission and in reflection.

FIG. 3 represents an overall diagram of a device operating both in transmission and reflection mode. An ultrasound transducer T2 or T3 is periodically excited such as to radiate an ultrasound wave into the propagation medium. This wave interacts with the propagation medium and it undergoes partial reflection and/or scattering. A part of the incident energy is reflected on entering the bone, a part of the energy transmitted into the bone is subsequently scattered by the internal structures of the latter, and in particular back-scattered to the emitter transducer T2 or T3. It is this same transducer (T2 or T3) which is used as a receiver for detecting the waves reflected by the bone and back-scattered by the internal architecture of the latter, and for converting them into an electrical signal which is subsequently amplified, digitized and transferred to the computer. The transducer T2 or T3 is electrically connected to the reception stage. The combined use in reflection of two transducers T2 and T3, placed opposite, makes it possible simultaneously to detect the echoes from two opposite faces of the bone. An automatic ultrasonic measurement of the thickness of the bone can thus be carried out. In addition, signal processing can be carried out subsequently on the back-scattered signals recorded by the transducers T2 or T3, in order to extract the acoustic parameters useful for characterizing the bone: attenuation as a function of frequency, back-scatter cross-section, texture parameter, etc.

In order to operate simultaneously in transmission and in reflection with two pairs of transducers placed opposite one another, use is preferably made of the solution illustrated by FIG. 3, according to which three pulse-generator stages are used to control the transducers T1, T'1, T2 and T3, the excitations being sequential in time: T1 emits first, when T'1 has detected the wave emitted by T1, T2 emits and it detects the reflected and back-scattered signals. Finally, T3 is excited in turn.

Another more economical but slower solution consists in using only a single common pulse generator for exciting the transducers T1, T'1, T2 and T3. In this case, it is sufficient to provide a switch in order to direct the excitation pulse to a different transducer at each shot. This switch is connected to the microprocessor which controls the switching. This variant has not been represented.

Figure 4:
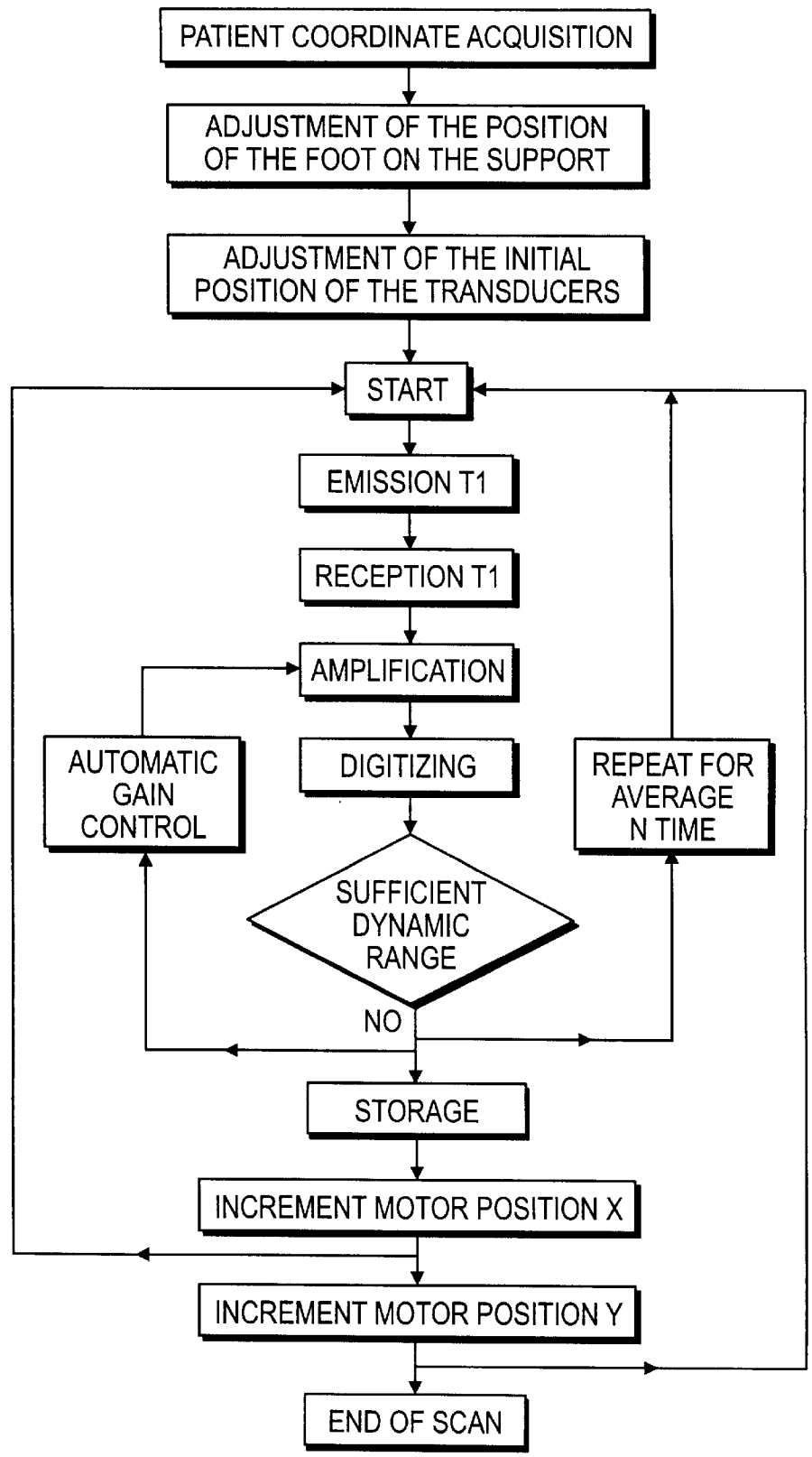
FIG. 4 is a diagram illustrating the principle of acquisition in transmission.

FIG. 4 represents the transmission acquisition diagram. The various steps in this acquisition are clearly seen on examining the figure.

Two solutions may be used for acquiring data in transmission and in reflection.

Figure 5:
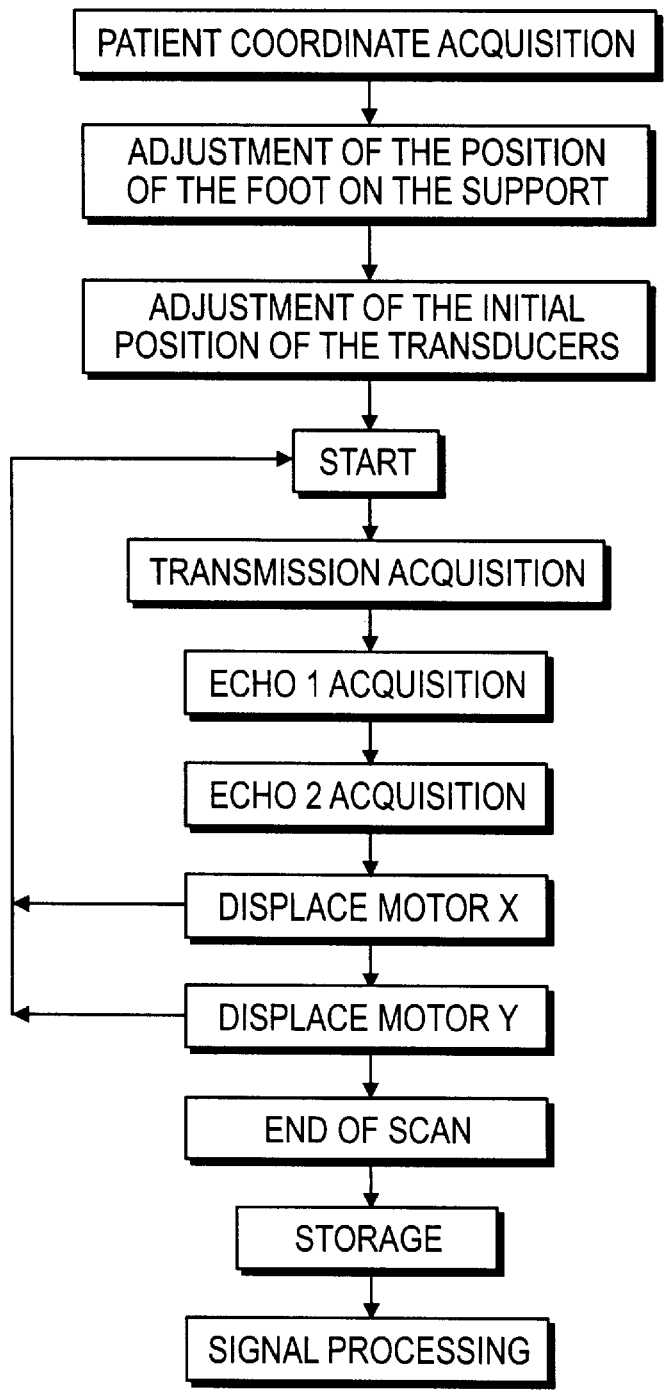
FIG. 5 is a diagram which illustrates the general principle of acquisition in transmission and in reflection.
Figure 6:
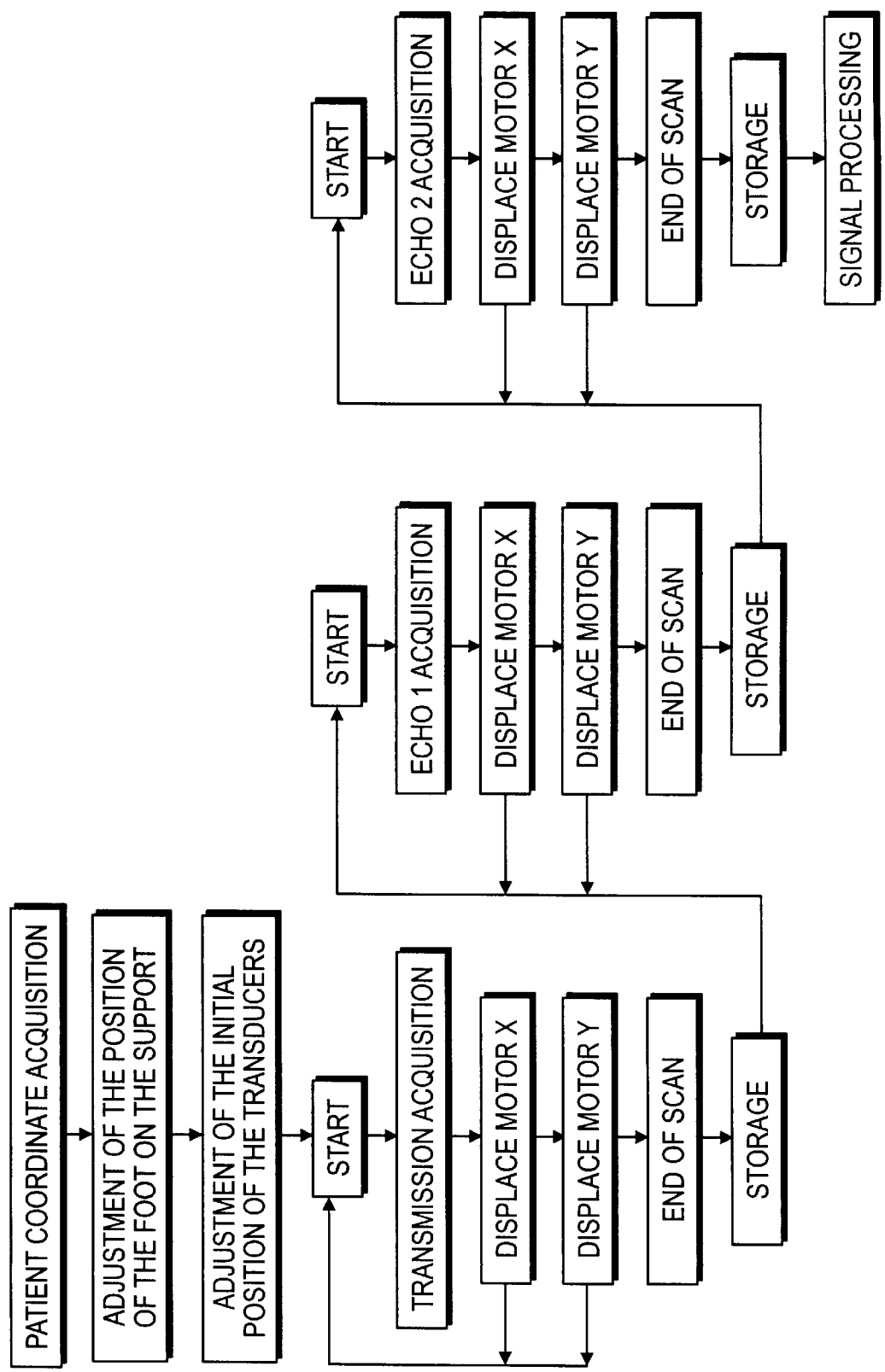
FIG. 6 is a diagram illustrating a variant of the acquisition mode in transmission and reflection.

In the first solution, illustrated by FIG. 5, the transmitted and reflected data are recorded during a single scan. For each position X, Y, transducers T1, T2, T3 are excited successively. In the second solution, illustrated by FIG. 6, the transmitted and reflected data are recorded during three different scans: the first scan is intended for acquisition of data by the pair of transducers T1 and T'1, and the second and third scans are intended of acquisition of data in reflection by the transducers T2 and T3.

It is possible to acquire a plurality of signals one after the other for a fixed position of the transducers. The signal/noise ratio is improved by means of these various acquisitions. In the event that this possibility exists, emission/reception is repeated as many times as is necessary. Once this acquisition sequence is completed, the position of the motors is incremented and the operation can be repeated.

As soon as the signal acquisition phase has been completed, all the digitized signals are stored in memory and the signal processing phase can then commence, either automatically or by means of a command initiated by the operator.

Figure 7:
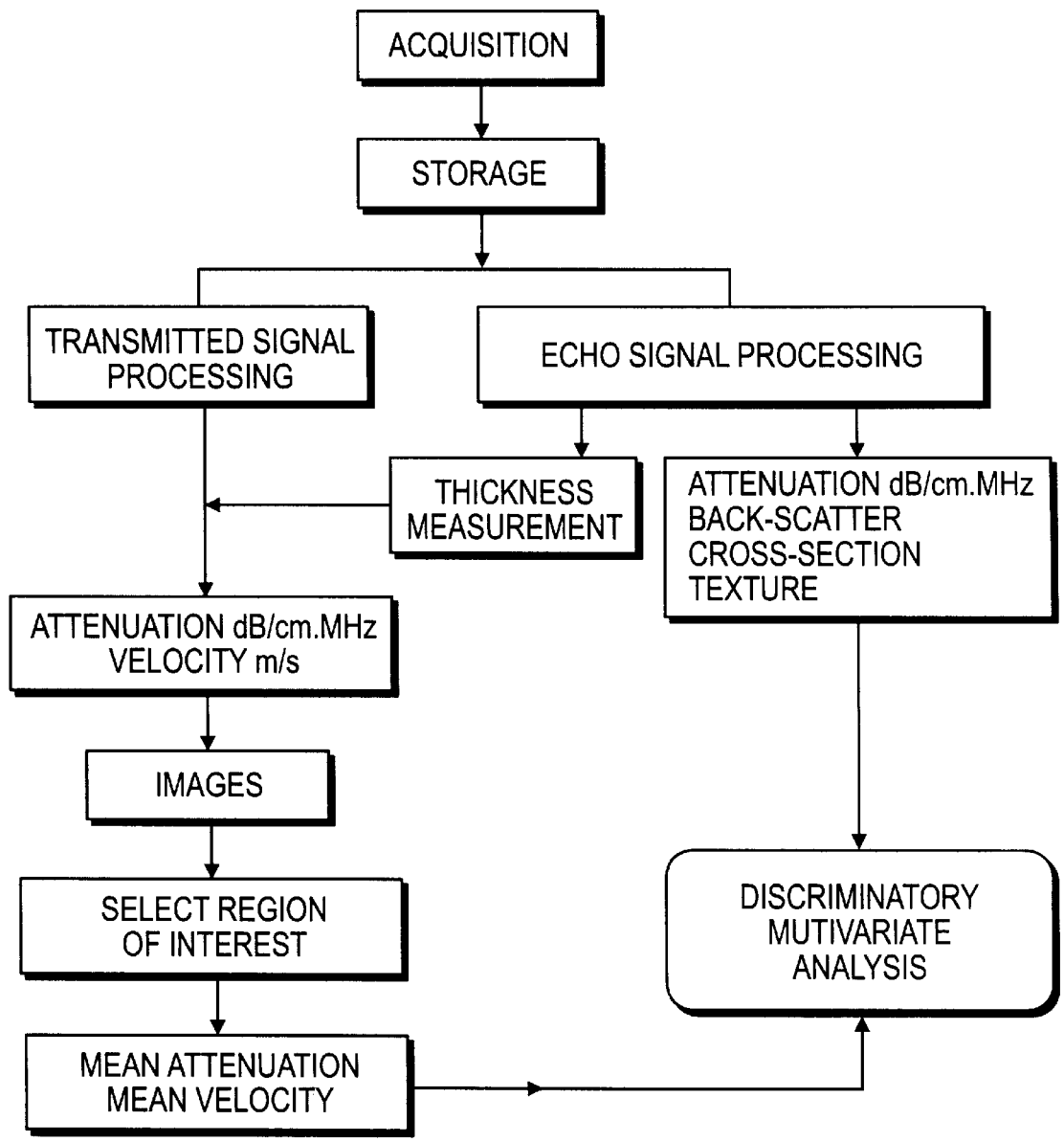
FIG. 7 is a block diagram illustrating the general principle of the signal processing and the method and the device forming the subject matter of the invention.

As has been specified hereinabove, the device implementing the present invention includes a signal processing module. The general principle of the signal processing is illustrated by the diagram in FIG. 7.

This signal processing module includes a computer, a bulk memory and a signal processing software package designed for analyzing the data previously acquired in transmission and/or in reflection. It includes a set of pre-programmed functions making it possible, in particular, to perform the following calculations:

calculation of the attenuation (in dB) as a function of frequency in transmission calculation of the attenuation coefficient as a function (in dB/MHz) of frequency in transmission calculation of the propagation times of the signals transmitted through the bone calculation of the bone thickness passed through at the measurement location calculation of the attenuation coefficient as a function of frequency (dB/cm.MHz) in transmission calculation of the propagation velocity of the ultrasound in transmission calculation of the attenuation (in dB) as a function of frequency in reflection calculation of the attenuation coefficient as a function of frequency (dB/cm.MHz) in reflection calculation of the back-scatter cross-section (in dB) as a function of frequency in reflection calculation of the back-scatter coefficient (dB/MHz) in reflection calculation of the integral back-scatter coefficient (dB.MHz) in reflection.

It is, of course, possible to add other signal-processing or image-processing functions which can provide quantitative information that is useful for characterizing the bone (texture analysis, for example).

The parameters are obtained for each position of the transducers, which makes it possible to obtain a parameter map. Image processing is included in the software, thus making it possible to select one or more regions of the measurement, having arbitrary shape, for estimation of a local mean of these parameters.

The method of estimating the parameters (attenuation and propagation velocity) in transmission relies on comparison of a reference signal with a signal transmitted through the bone.

The reference signal is a signal which has propagated through a medium, the acoustic characteristics (attenuation and velocity) of which are well known (water, in this exemplary embodiment). The reference signal and the signals transmitted through the bone are recorded under the same conditions. For example, the reference signal may be acquired either when starting the apparatus, or before each examination. It is also possible to record a single reference and store it in the memory of the computer in order to recall it subsequently on each examination.

A description will now be given by way of example of various signal processing modes for certain functions carried out by the method of the invention.

1. Estimation of the propagation velocity in transmission.

Figure 8:
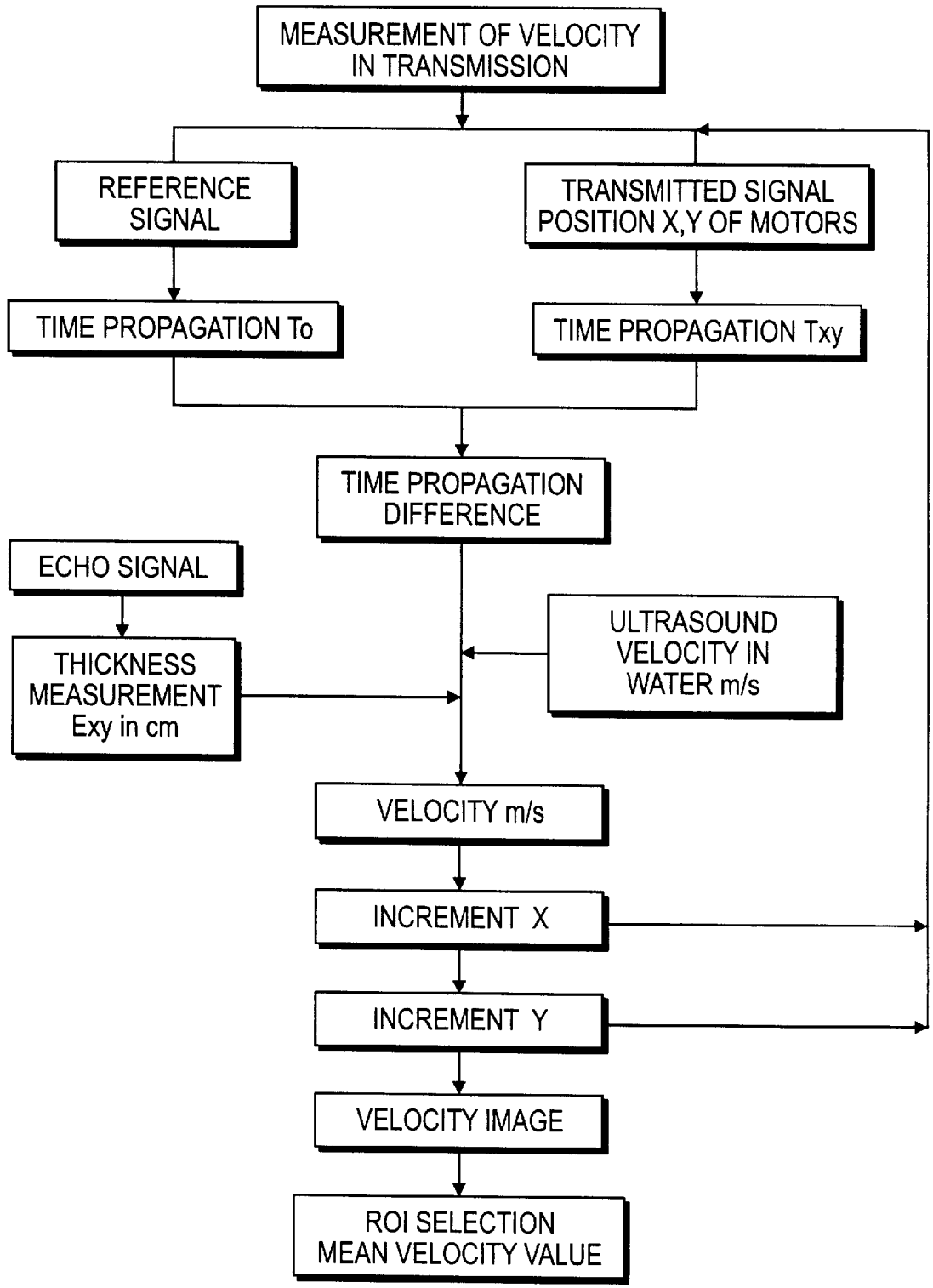
FIG. 8 is a diagram illustrating the processing of the transmitted signal with a view to measuring the propagation velocity of the ultrasound wave in bone.

The principle of processing the transmitted signal in order to measure this velocity is illustrated by the diagram in FIG. 8. This processing mode therefore includes the following steps:

the transducers are at the position X, Y;

The transducer T1 emits and the wave thus emitted, transmitted through the bone, is detected by the receiver transducer T'1, then amplified, digitized and transferred to the computer. Of course, and as specified hereinabove, for measurements through the calcaneus, the transducers and the bone are placed in a bath, the temperature of which is controlled by a thermostat (see FIG. 1). This first measurement is intended for estimating the propagation time of the wave transmitted through the bone and for calculating the difference between this time and that of the reference signal;

the transducer T2 (or T1) emits and the transducer T2 (or T1) receives the signal thus emitted and reflected by the bone. The reflected ultrasound wave is amplified, digitized and transferred to the computer.

the duration of the propagation time of the echo which is reflected by the entry face of the bone, facing the transducer T2 (or T1), is estimated;

the transducer T3 (or T'1) emits and the transducer T3 (or T'1) receives the signal reflected by the bone. The reflected wave is amplified, digitized and transferred to the computer;

the duration of the propagation time of the echo reflected by the entry face of the bone, which is turned towards T3 (or T'1), is estimated;

these latter two measurements are intended for calculating the thickness of the calcaneus at the location of the measurement. The propagation velocity in transmission of the ultrasound wave is deduced in a known manner from the propagation time of the wave between the two transducers. In order to estimate the propagation velocity, it is necessary to know the thickness of the bone and this, according to the invention, is measured by ultrasound.

Figure 9:
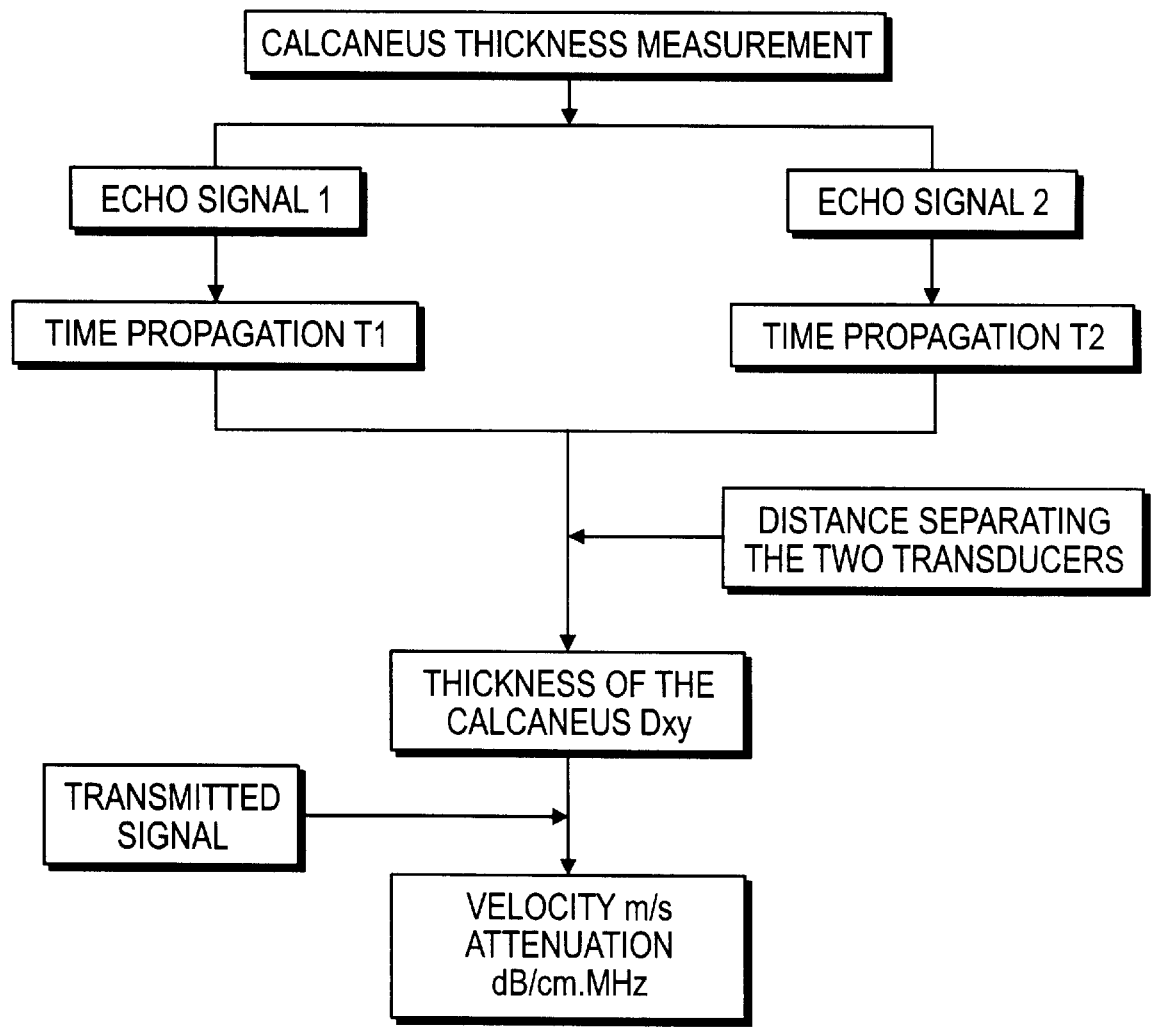
FIG. 9 is another diagram illustrating the processing of the signal, in echographic mode, with a view to measuring the thickness of bone.

FIG. 9 illustrates the principle of processing the principle of processing the echographic signal in order to measure this thickness. In fact, using echography, it is possible to determine the distance separating a transducer from the face of the bone, (face of interest). It is sufficient to identify the echo from this face and to measure its propagation time. Each transducer T2 and T3 (or T1 and T'1) is interrogated in turn in echographic mode, and the propagation time T1 and T2 of the echoes reflected by each of the opposite lateral faces of the bone are measured. The thickness of the bone is deduced therefrom.

2. Estimation of the attenuation coefficient in transmission.

Figure 10:
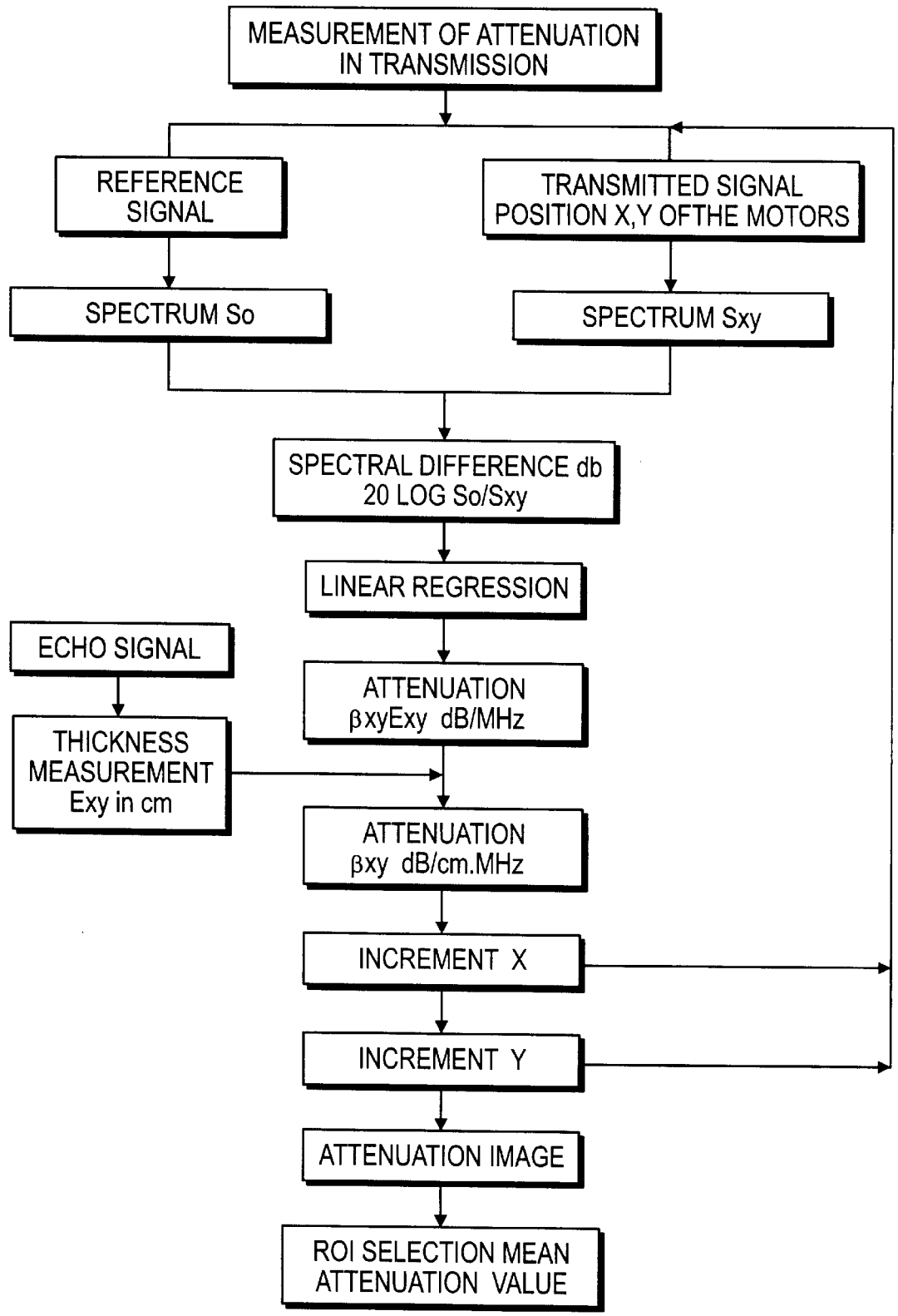
FIG. 10 is a block diagram illustrating the principle of the processing of the transmitted signal for measuring attenuation.

The principle of the signal processing according to this particular mode is illustrated by FIG. 10. It includes the following steps:

the transducers are initially in the position X, Y;

the transducer T1 emits and the wave transmitted through the bone is detected by the receiver transducer T'1, then it is amplified, digitized and transferred to the computer. As before, for measurements through the calcaneus, in this embodiment, the transducers and the bone are placed in a bath, the temperature of which is controlled by a thermostat (FIG. 1);

the frequency spectra of the signal transmitted through the bone and of the reference signal are calculated. The attenuation as a function of frequency is obtained by comparing the spectrum of a reference signal recorded in water with that of the signal transmitted through the bone. The ultrasound signal is of the pulse type and it includes a plurality of frequencies in the interval between 0.2 MHz and 1 MHz.

In order to overcome variations connected with the thickness of the calcaneus, it is necessary to compare the attenuations normalized to the exact thickness (dB/MHz.cm) of the calcaneus at the measurement point. The manner according to which an ultrasonic thickness measurement can be carried out in echographic mode was explained hereinabove.

As in the case of all heterogeneous media, the value of the acoustic parameters depends on the location where the measurement is taken. The scanning device of the apparatus according to the invention makes it possible to explore the entire bone volume and to obtain a parameter map. On the basis of the images of attenuation as a function of frequency and of velocity of the ultrasound wave, it is possible to select a measurement region (region of interest) and to estimate a mean of the parameters in this region. The software comprises some simple image-processing functions, in particular for selecting measurement regions of variable shape and size. The support of the image is used for selecting identical measurement regions in different patients or during repeated measurements in a single patient.

The invention thus makes it possible to obtain, in particular, ultrasound imaging of the calcaneus (attenuation and velocity images) by virtue of using focused transducers, the images thus obtained being comparable with those obtained by a scanner.

3. Estimation of the attenuation coefficient and of the back-scatter cross-section in reflection, as a function of frequency.

The various steps in this mode of processing the transmitted signals are the following:

the transducers are at the position X and Y;

the transducer T2 (or T3, or T1, or T'1) emits;

the transducer T2 (or T3, or T1, or T'1) receives the echographic signal back-scattered by the internal architecture of the bone, this signal being subsequently amplified, digitized and transferred to the computer.

a sliding spectral analysis of the echographic signal is carried out, and the spectra are estimated as a function of depth;

the spectral centroids are calculated as a function of depth;

the attenuation coefficient is calculated as a function of frequency (dB/cm.MHz) in reflection;

the spectral difference between the spectrum of the signal and a reference spectrum is calculated, then the back-scatter cross-section (in dB) is calculated as a function of frequency in reflection;

the back-scatter coefficient (dB/MHz) in reflection is calculated; and the integral back-scatter coefficient (dB.MHz) in reflection is calculated. Scanning the ultrasound beam makes it possible to explore the entire bone volume. The attenuation and back-scatter coefficients are calculated for each position of the transducers. It is then possible to estimate a local average of the parameters within a region of interest selected by the operator.

The attenuation can be estimated on the basis of the sampled radio-frequency echographic signal. The principle of calculating the attenuation relies on time/frequency analysis of the echographic signal.

The invention thus makes it possible to measure the back-scatter cross-section as a function of frequency. It is known that the physical properties of bone tissue are indeed demonstrated by this measurement.

It results from reading the above description that the invention provides a solution to the difficulties posed by employing bone-analysis ultrasound apparatus currently on the market:

the device for automatically scanning the ultrasound beam makes it possible to solve the problem of accurate positioning of the bone and of positioning of the measurement region or region of interest;

the use of focused transducers makes it possible to obtain high-quality images;

it makes it possible to obtain ultrasound measurements in transmission through the bone and in reflection;

it makes it possible to collect and process signals reflected and/or scattered by the internal architecture of the bone, which provides information in addition to that already found in the signals which have been transmitted through the bone. The method and the device forming the subject matter of the invention thus provide much more information than is provided with devices according to the prior art, while offering better accuracy, reproducibility and sensitivity.

Among the fields of application of the invention, osteoporosis was specified hereinabove. In this application, the invention provides a non-traumatic physical method for in vivo evaluation of the bone quality (mass, rigidity, architecture). The risk of fracture associated with a decrease in the strength of the bones can thus be assessed quantitatively, this decrease being, as is known, a consequence of the phenomena of the demineralization and bone architecture modification encountered in osteoporosis.

The description given hereinabove of exemplary embodiments of the invention is not limited to measurements of the calcaneus and of the patella: there are, of course, other fields of application of the invention, particularly with a view to monitoring the degree of mineralization of the skeleton, in particular in order to follow the evolution of the bone architecture or of the elasticity of the bone structure. Among these applications, mention may be made, in particular, of:

skeletal maturation in neonates;

secondary osteoporosis, osteomalacia, etc.;

monitoring of racehorses;

in vitro characterization of bone parts.

It remains clear that the present invention is not limited to the modes of implementation nor to the exemplary embodiments described and/or represented here, but that it encompasses all variants thereof. Thus, the exemplary embodiment described here refers to measurements carried out in immersion. However, without departing from the scope of the present invention, the measurements may be carried out by contact, using an array of transducers and a coupling medium, it being possible to scan the ultrasound beam electronically.

We claim:

1. A method for the in-vivo evaluation of the mechanical and architectural properties of bones, by propagating an ultrasound wave through the bone and subsequently studying the interaction of the wave with the bone, to obtain parametric images of attenuation, reflection, and back-scattering, comprising the steps:

emitting an ultrasound beam from at least a single focused transducer through a bone;

scanning the bone with the beam in a plane that is orthogonal to the direction of ultrasound propagation;

receiving signals transmitted through the bone in response to the scanning;

receiving signals reflected by faces of the bone in response to the scanning;

receiving signals backscattered by internal structures of the bone in response to the scanning;

storing the three aforementioned signals;

processing the stored signals for calculating the
a) propagation velocity of the ultrasound beam in the bone;
b) thickness of the bone;
c) transmission attenuation coefficient of the ultrasound beam;
d) and the reflection parameters for estimating back-scatter and attenuation coefficients; and obtaining parametric images of attenuation, reflection and backscattering from calculations derived from processed stored signals.

2. The method according to claim 1, wherein at leased one focused transducer, operates at multiple frequencies, to produce parametric images of transmission attenuation as a function of frequency and propagation velocity of the ultrasound beam transmitted through a bone.

3. The method according to claim 1, wherein at least one focused transducer, operates at multiple frequencies, to produce reflection images of the ultrasound beam reflected from a bone.

4. The method set forth in claim 1 wherein a plurality of transducers are operated at multiple frequencies to produce, from the calculations:

reflectivity images from transducers functioning in a reflection mode;

estimates of attenuation and/or backscatter coefficients, selectively, as a function of the frequency of a reflected ultrasound beam; and parametric images of attenuation as a function of frequency and of propagation velocity from transducers functioning in a transmission mode.

5. The method set forth in claim 1 wherein a plurality of ultrasound transducers are arranged in an array and operated sequentially to electronically scan.

* * * * *